United States Patent

Bovy et al.

Patent Number: 5,453,440
Date of Patent: Sep. 26, 1995

[54] PEPTIDE MIMICS USEFUL AS PLATELET AGGREGATION INHIBITORS

[75] Inventors: Philippe R. Bovy, St. Louis, Mo.; Robert B. Garland; Masateru Miyano, both of Northbrook, Ill.; Joseph G. Rico, Manchester; Thomas E. Rogers, Ballwin, both of Mo.; Jeffery A. Zablocki, Skokie, Ill.

[73] Assignee: G. D. Searle & Co., Chicago, Ill.

[21] Appl. No.: 138,559

[22] Filed: Oct. 15, 1993

Related U.S. Application Data

[63] Continuation of Ser. No. 847,260, Mar. 6, 1992, abandoned.

[51] Int. Cl.$^6$ ................................. A61K 31/235
[52] U.S. Cl. ................ 514/533; 514/419; 514/535; 514/538; 514/539; 514/563; 514/542; 548/495; 560/21; 560/35; 562/435; 562/440
[58] Field of Search ............... 560/21, 35; 562/435, 562/440; 548/495; 514/533, 535, 563, 419, 542, 538, 539

[56] References Cited

U.S. PATENT DOCUMENTS 5,273,982  12/1993  Alig ................................. 514/316

FOREIGN PATENT DOCUMENTS 381033   8/1990  European Pat. Off. .
445796   9/1991  European Pat. Off. .

OTHER PUBLICATIONS

U.S. Ser. No. 07/777,811, filed Oct. 15, 1991, Philippe Bovy.
U.S. Ser. No. 07/777,875, filed Oct. 15, 1991, Philippe R. Bovy.

*Primary Examiner*—Michael L. Shippen
*Attorney, Agent, or Firm*—Cynthia S. Kovacevic; Roger A. Williams

[57] ABSTRACT

This invention relates to compounds having the following formula

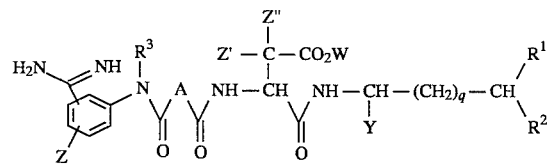

or pharmaceutically acceptable salt thereof which are useful in the inhibition of platelet aggregation, to pharmaceutical compositions of such phenylamidines derivatives, and to a method of inhibiting platelet aggregation in mammals by administering such compounds and compositions.

14 Claims, No Drawings

PEPTIDE MIMICS USEFUL AS PLATELET AGGREGATION INHIBITORS

This is a continuation of application Ser. No. 07/847,260, filed Mar. 6, 1992, now abandoned.

FIELD OF THE INVENTION

The present invention relates to pharmaceutical agents (compounds) which inhibit platelet aggregation in mammals.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gp IIb/IIIa; this is an important feature of the platelet function. Inhibitors of this interaction are useful in modulating platelet thrombus formation.

It is also known that another large glycoprotein named fibronectin, which is a major extracellular protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Haverstick et al., Blood 66 (4), 946–952 (1985); and Ruoslahti and Pierschbacher, *Science* 238, 491–497 (1987). Still other such inhibitory peptides are disclosed in European Patent Applications 275,748 and 298,820.

European Patent Application 445,796 discloses acetic acid derivatives which have inhibitory action on the bonding of adhesive proteins to blood platelets as well as on blood platelet aggregation and cell-cell adhesion.

European Patent Application 372,486 discloses N-acyl beta amino acid derivatives and their salts. Said compounds are useful for inhibiting platelet aggregation in the treatment of thrombosis, stroke, myocardial infarction, inflammation and arteriosclerosis, and for inhibiting metastasis.

European Patent Application 381,033 discloses amidino or guanidinoaryl substituted alkanoic acid derivatives useful for the treatment of thrombosis, apoplexy, cardiac infarction, inflammation, arteriosclerosis and tumors.

SUMMARY OF THE INVENTION

The present invention relates to a class of compounds represented by the formula:

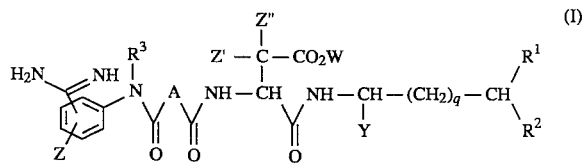

or a pharmaceutically acceptable salt thereof, wherein $R^1$, $R^2$ and $R^3$ are independently selected from the group consisting of hydrogen; alkyl having 1 to 6 carbon atoms; phenyl; substituted phenyl wherein each substituent can be selected from the group consisting of alkyl having 1 to 6 carbon atoms, halogen, alkoxy having 1 to 6 carbon atoms, trifluoromethyl, hydroxy, nitro and carboxyl; and a 5- or 6-membered heterocyclic ring fused to a benzene ring wherein the hetero atom is selected from the group consisting of nitrogen, oxygen and sulfur;

A is selected from the group consisting of a lower alkyl having 1 to 6 carbon atoms, a lower alkenyl or alkynyl having 2 to 6 carbon atoms and a cycloalkyl having 3 to 6 carbon atoms, the alkyl, alkenyl, alkynyl or cycloalkyl optionally substituted by phenyl or phenyl substituted by halogen or hydroxy;

W is selected from the group consisting of hydrogen, methoxyalkyl, lower alkyl having 1 to 6 carbon atoms, and cycloalkyl having 3 to 6 carbon atoms;

Y is selected from the group consisting of hydrogen, carboxyl and alkoxycarbonyl having 1 to 6 carbon atoms;

Z, Z' and Z" are independently selected from the group consisting of halogen, alkoxy having 1 to 6 carbon atoms, alkyl having 1 to 6 carbon atoms, trifluoromethyl, hydrogen and hydroxy; and q is an integer from 0 to 3;

with the proviso that if A is propyl or methyl and q is 0 then $R^1$ and $R^2$ are other than phenyl.

It is another object of the invention to provide pharmaceutical compositions comprising compounds of the formula I. Such compounds and compositions have usefulness as modulators and/or inhibitors of platelet aggregation. The invention also relates to a method of therapeutically inhibiting or modulating platelet aggregation in a mammal in need of such treatment.

DETAILED DESCRIPTION OF THE INVENTION

The present invention relates to a class of compounds represented by the formula I, described above.

A preferred embodiment of the present invention is a compound of the formula:

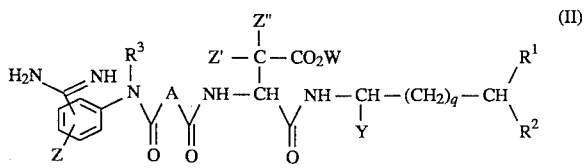

or a pharmaceutically acceptable salt thereof, wherein $R^1$, $R^2$ and $R^3$ are independently selected from the group consisting of hydrogen; alkyl having 1 to 6 carbon atoms; phenyl; and substituted phenyl wherein each substituent can be selected from the group consisting of alkyl having 1 to 6 carbon atoms, halogen, alkoxy having 1 to 6 carbon atoms, trifluoromethyl, hydroxy, nitro and carboxyl;

A is selected from the group consisting of a lower alkyl having 1 to 6 carbon atoms, a lower alkenyl or alkynyl having 2 to 6 carbon atoms and a cycloalkyl having 3 to 6 carbon atoms, the alkyl, alkenyl, alkynyl or cycloalkyl optionally substituted by phenyl or phenyl substituted by halogen or hydroxy;

W is selected from the group consisting of hydrogen, methoxyalkyl, lower alkyl having 1 to 6 carbon atoms, and cycloalkyl having 3 to 6 carbon atoms;

Y is selected from the group consisting of hydrogen, carboxyl and alkoxycarbonyl having 1 to 6 carbon atoms;

Z, Z' and Z" are independently selected from the group consisting of halogen, alkoxy having 1 to 6 carbon atoms, alkyl having 1 to 6 carbon atoms, trifluoromethyl, hydrogen and hydroxy; and q is an integer from 0 to 3;

with the proviso that if A is propyl or methyl and q is 0 then $R^1$ and $R^2$ are other than phenyl.

Exemplifying this embodiment are the following compounds:

N-[N-[4-[[4-(aminoiminomethyl)phenyl] amino-1,4-dioxobutyl]-L-α-aspartyl]-L-phenylalanine, 1-methyl ester;

N-[N-[4-[[4-(aminoiminomethyl)phenyl] amino]-1,4-dioxobutyl]-L-α-aspartyl]-L-phenylalanine; and N-[N-[4-[[4-(aminoiminomethyl)phenyl] (phenylmethyl)amino]-1,4-dioxobutyl]-L-alpha-aspartyl]-L-phenylalanine.

As used herein, the term "lower alkyl" refers to a straight chain or branched chain hydrocarbon radical having from 1 to 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein, the term "lower alkoxy" includes straight or branched chain lower alkyl ether radicals wherein the term lower alkyl is as defined above. Examples of such groups are methoxy, ethoxy, n-propoxy, n-butoxy, isobutoxy, t-butoxy, sec-butoxy, isopropoxy and the like.

As used herein the term "halogen" refers to chloro (CL), fluoro (F), bromo (Br) or iodo (I).

As used herein the term "lower alkenyl" refers to unsaturated acyclic hydrocarbons containing at least one double bond and 2 to 6 carbon atoms. Examples of such groups are ethenyl, propenyl, butenyl, isobutenyl, pentenyl, hexenyl and the like.

As used herein the term "alkynyl" refers to acyclic hydrocarbons containing one or more triple bonds and 2 to 6 carbon atoms. Examples of such groups are ethynyl, propynyl, butynyl, pentynyl, hexynyl and the like.

As used herein, the term "lower alkylene" refers to a straight chain or branched chain divalent hydrocarbon radical having from 1 to 6 carbon atoms. Examples of such alkylene radicals are methylene, ethylene, and the like.

As used herein the term "lower alkenylene" refers to unsaturated acyclic bivalent hydrocarbons containing at least one double bond and 2 to 6 carbon atoms. Examples of such groups are and the like.

As used herein the term "alkynylene" refers to acyclic bivalent hydrocarbons containing one or more triple bonds and 2 to 6 carbon atoms. Examples of such groups are and the like.

As used herein the term "5- or 6-membered heterocyclic ring fused to a benzene ring wherein the hetero atom is selected from nitrogen, oxygen or sulfur" refers to a group composed of two fused rings wherein one ring is benzene and the other ring comprises 5 or 6 carbon atoms wherein one of the carbon atoms is replaced by nitrogen, oxygen or sulfur. Illustrative of such groups are indolyl, benzofuranyl, benzothiopyranyl, chromenyl and the like.

As used herein the term "alkoxycarbonyl" having 1 to 6 carbon atoms refers to the

ROCO— group wherein the R represents alkyl having 1 to 6 carbon atoms. Illustrative of such groups are methoxycarbonyl, ethoxycarbonyl, propanoxycarbonyl, pentanoxycarbonyl and the like.

The term "cycloalkyl" as used herein means an alicyclic radical with 3 to 6 carbon atoms. Examples of suitable cycloalkyl radicals include cyclopropyl, cyclopropenyl, cyclobutyl, cyclopentyl, cyclohexyl, 2-cyclohexen-1-yl, and the like.

The compounds as shown in Formula I & II can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of the pharmacologically acceptable salts may be prepared by conventional means. (See Berge et al., *J Pharm. Sci.*, 66(1), 1–19 (1977) for additional examples of pharmaceutically acceptable salts.)

This invention also relates to a method of inhibiting platelet aggregation and more specifically, a method of treatment involving the administration of compounds of Formula I to achieve such inhibition.

For the inhibition of platelet aggregation, compounds of the present invention may be administered orally, parenterally, or by inhalation spray, rectally, or topically in dosage unit formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus the dosage regimen may vary widely. Dosage levels of the order from about 0.01 mg to about 150 mg per kilogram of body weight per day are useful in the treatment of the above-indicated conditions.

For oral administration, the pharmaceutical composition may be in the form of, for example, a tablet, capsule, suspension or liquid. The pharmaceutical composition is preferably made in the form of a dosage unit containing a particular amount of the active ingredient. These may contain, for example, an amount of active ingredient from about 1 to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The compounds of formula I may be prepared by standard synthetic methods combined with methods analogous to solution phase peptide synthesis [see: "The Peptides: Analysis, Synthesis, Biology" (E. Gross and J. Meienhofer, eds.), Vol. 1–5, Academic Press, New York)].

Three general synthetic sequences are outlined in Schemes I–III.

In Scheme I, the aminobenzamidine 1 (i.e., Z is hydrogen in Formula I) is coupled to an alkanoic, alkenoic (both substituted or not) or alkynoic diacid. An activated form of the diacid is preferentially used. These activated forms include anhydrides, internal anhydrides, acid chlorides or one of the various activated forms as described in *Principles of Peptide Synthesis*, Bodansky, 1984, Springer-Verlag. A highly preferred procedure involves the condensation of an anhydride (e.g. succinic anhydride 2) with a salt of amino benzamidine 1. The reaction is best conducted in a polar solvent such as methylene chloride, acetonitrile, dioxane, dimethylformamide, dimethylsulfoxide or a mixture of such solvents in the presence of an acid binding agent such as sodium, potassium or cesium carbonate, triethylamine, pyridine, sodium hydride, dimethylaminopyridine, diazabicycloundecene, or a mixture of such agents, at temperatures ranging between 0° C. and 120° C. The final compounds are obtained by coupling of the amidine derivative 3 with a properly protected aspartic derivative. The amide bonds are formed using standard coupling reagents, e.g. dicyclohexylcarbodiimide (DCC), carbonyldiimidazole, disuccinimidyl carbonate (DSC), benzotriazol-1-yl-oxy-tris-(dimethylamino)-phosphonium hexafluorophosphate (BOP) or isobutyl chloroformate (mixed anhydride method). When the α-aspartic derivative used in the coupling is protected as an ester of the beta carboxylic acid function (4, W=alkyl, aryl, ...), the free acids 5 are obtained by a suitable deprotection method as described by T. H. Greene in *"Protective Groups in Organic Synthesis"*, Wiley Interscience, 1980.

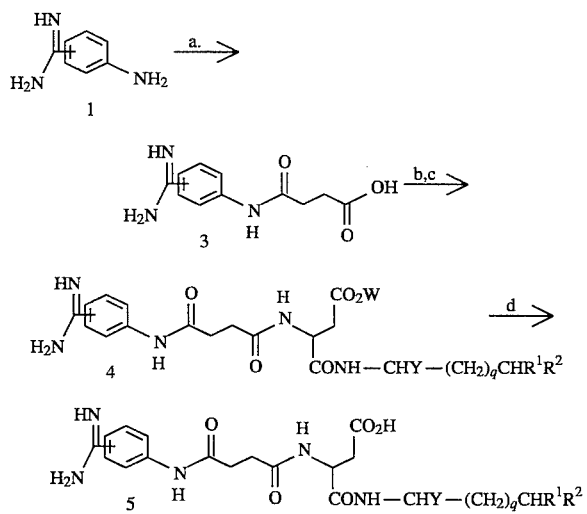

SCHEME I a. Succinic anhydride (2), pyridine, DMAP.
b. i-ButOCOCl, NMM.
c. Aspartame derivative
d. NaOH or LiOH.

Wherein, W, $R^1$, $R^2$ have the meanings described in Formula I.

Scheme II illustrates an alternate route of synthesis. An aminobenzonitrile 6 can be used for condensation with the desired diacid or diacid derivative. In Scheme II the nitrile can be converted to the amidine directly or at a later stage. When the aminobenzonitrile is used in the condensation reaction, the cyano group of the resulting intermediate 7 is converted to the amidine 8 via the thioimidate in nearly quantitative yield. The thioimidate is formed by first treating the cyano compound with hydrogen sulfide ($H_2S$) followed by alkylation with methyl iodide. Next, treatment of the thioimidate with ammonium acetate affords the amidine as the salt (HI). Alternatively, the nitrile 7 can be converted to the amidine by the use of lithium bis(trimethylsilyl)amide in an inert solvent such as diethyl ether (R. T. Boeré et al., *J. Organomet. Chem.*, 331, 161–67, 1987). The desired compounds are obtained by coupling of the amidine derivative 8 with a properly functionalized β-aspartic derivative. The amide bonds are formed using standard coupling reagents as described above for Scheme I.

SCHEME II

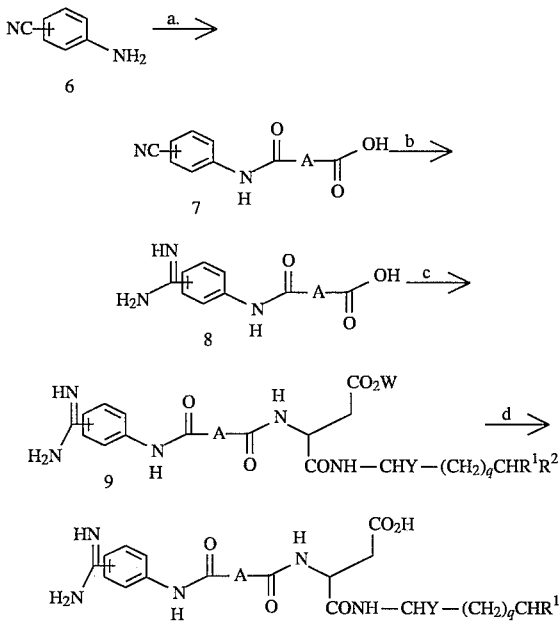

a. Activated diacid.
b. H2S,pyridine; MeI, acetone; NH4OAc or Hexamethyl disilazane in diethyl ether.
c. Anhydride mixte, NMM.
c. Aspartame derivatives.
d. Base or acid.

Wherein, A, W, $R^1$, $R^2$ have the meanings described in Formula I.

Scheme III, is described the obtention of derivatives of formula I using the amino nitriles as starting materials. The cyano group is kept intact as a precursor for the amidine function throughout two amide bond forming steps. The first intermediate 10 is directly engaged in a reaction with the desired aspartic derivative. The intermediate 10 is then converted to the benzamidine. A method of choice to produce the amidine function is via the thioimidate procedure as described in Scheme II. It is desirable, in Scheme III to prepare the intermediate 11 as an ester. The most desirable ester is the t-butyl ester which can be deprotected to the acid by contact with a strong acidic medium such as HBr/AcOH or trifluoroacetic acid/dichloromethane.

SCHEME III

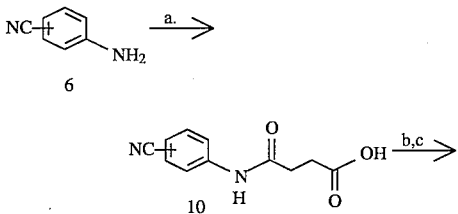

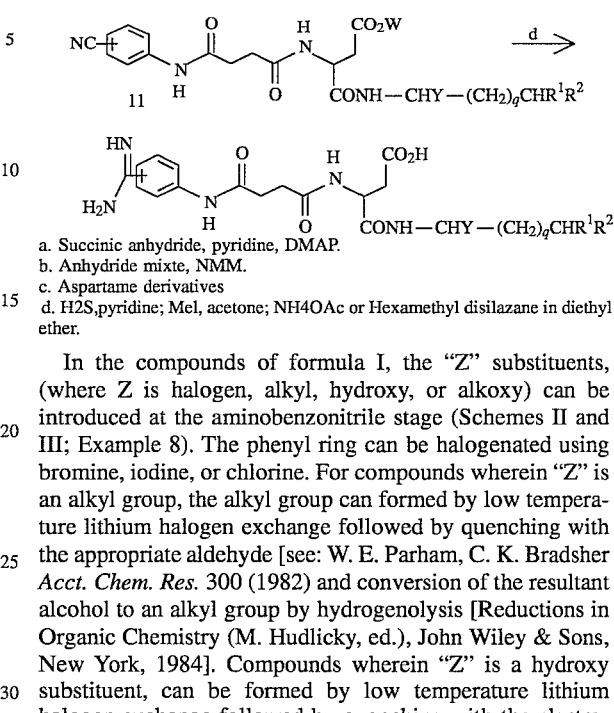

a. Succinic anhydride, pyridine, DMAP.
b. Anhydride mixte, NMM.
c. Aspartame derivatives
d. H2S,pyridine; MeI, acetone; NH4OAc or Hexamethyl disilazane in diethyl ether.

In the compounds of formula I, the "Z" substituents, (where Z is halogen, alkyl, hydroxy, or alkoxy) can be introduced at the aminobenzonitrile stage (Schemes II and III; Example 8). The phenyl ring can be halogenated using bromine, iodine, or chlorine. For compounds wherein "Z" is an alkyl group, the alkyl group can formed by low temperature lithium halogen exchange followed by quenching with the appropriate aldehyde [see: W. E. Parham, C. K. Bradsher *Acct. Chem. Res.* 300 (1982) and conversion of the resultant alcohol to an alkyl group by hydrogenolysis [Reductions in Organic Chemistry (M. Hudlicky, ed.), John Wiley & Sons, New York, 1984]. Compounds wherein "Z" is a hydroxy substituent, can be formed by low temperature lithium halogen exchange followed by quenching with the electrophilic bis(trimethylsilyl)peroxide ((TMSO)$_2$) [M. Taddei and A. Ricci *Synthesis* 633–635 (1986)] which affords a silyl ether which can be converted to a hydroxy group by treatment with hydrochloric acid [M. Taddei and A. Ricci ibid]. Compounds wherein "Z" is an alkoxy substituent (OR) can be formed by treating the derivative where "Z" is a hydroxy group with a weak base (K$_2$CO3) and an appropriate alkyl halide [R-Hal, 2 equivalents, see: C. F. H. Allen and J. W. Gates,*J.Organic Syntheses Coll.* Vol. 3 (140) (1955)]which will form the ester as well. The ester can be selectively cleaved in the presence of the ether with one equivalent of sodium hydroxide.

The derivative where $R^1$ is other than hydrogen can be obtained by using an appropriately substituted aminobenzamidine. For example, the 4-[N(phenylmethyl)]aminobenzamidine can be reacted with succinic anhydride in a manner similar to the amino benzamidine (see Example 9).

Purification of final compounds is usually by reverse phase high pressure liquid chromatography [*High Performance Liquid Chromatography Protein and Peptide Chemistry*, F. Lottspeich, A. Henscher, K. P. Hupe, eds., Walter DeGruyter, New York, 1981]or crystallization.

Contemplated equivalents of the platelet aggregation inhibitors, derivatives and intermediates of the formulas set forth above include compounds having the same general properties, wherein one or more of the various R groups are simple variations of the substituents as defined herein, e.g., wherein R is a higher alkyl group than that indicated. In addition, where a substituent can be a hydrogen, a substituent other than hydrogen can be introduced at that position, e.g., a hydrocarbon radical or a halogen, hydroxy, amino and the like, as long as the overall activity and/or synthesis procedure is not affected.

The chemical reactions described above are generally disclosed in terms of their broadest application to the preparation of the compounds of this invention. Occasionally, the reactions may not be applicable as described to each compound included the disclosed scope. The compounds for which this occurs will be readily recognized by those skilled in the art. In all such cases, either reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention.

The following examples are provided to illustrate the present invention and are not intended to limit the scope thereof. Those skilled in the art will readily understand that known variations of the conditions and processes of the following preparative procedures can be used to prepare the compounds of the present invention.

EXAMPLE 1

N-[N-[4-[[4-(aminoiminomethyl)phenyl]amino]-1,4-dioxobutyl]-L-alpha-aspartyl]-L-phenylalanine, 1-m ethyl ester

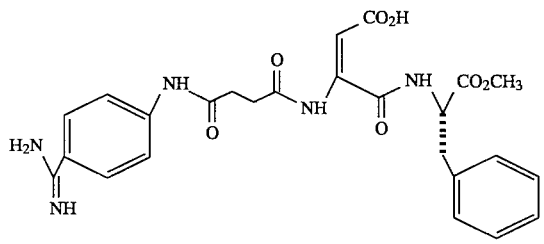

Step 1. Preparation of 4-[[4-(aminoiminomethyl)phenyl]amino]-4-oxo-butanoic acid Aminobenzamidine di-HCl (25 g, 120 mmol) was added to dry DMF (100 ml). To this solution dry pyridine (100 ml) and succinic anhydride (12 g, 120 mmol) followed by dimethylaminopyridine (DMAP 1.5 g 0.012 mmol) were added. The product precipitated after heating for ½ h at 100° C. The product was filtered, washed with water, acetonitrile and ether. The white solid was suspended in dioxane, 4N HCl in dioxane (100 ml) was added and the suspension was stirred for 1 h, filtered and dried in a desiccator to give 28 g, 88% of 4-[[4-(aminoiminomethyl)phenyl]-amino]-4-oxobutanoic acid as a white yellow solid which decomposes between 270° and 290° C.

Step 2. Preparation of N-[N-[4-[[4-(aminoiminomethyl)phenyl]-amino]-1,4-dioxobutyl]-L-alpha-aspartyl]-L-phenylalanine, 1-methyl ester 4-[[4-(aminoiminomethyl)phenyl]amino]-4-oxobutanoic acid hydrochloride prepared in Example 1, Step 1 (3.0 g, 11 mmol) was added to dry DMF (225 ml) followed by N-methylmorpholine (1.2 g, 11 mmol) and isobutyl chloroformate (1.5 g, 11 mmol) at 25° C. The mixture was stirred for 5 min. Aspartame (available from Sigma;A-5139; equivalent) was added followed by dimethylaminopyridine. After 1 h the solvent was removed under reduced pressure and the product purified by reverse phase chromatography (water/acetonitrile) to result in 2.2 g of a white solid: 1H NMR (d6-DMSO) δ2.47 (m, 4H), 2.65 (m, 3H), 2.97 (m, 2H), 3.55 (s, 3H), 4.45 (m, 1H), 4.58 (m, 1H), 7.79 (s, 4H), 7.99 (d, 1H, J=8.09 Hz), 9.1 (bs, 2H), 9.19 (bs, 2H), 10.42 (s, 1H); MS (FAB) M/e 512.3 (M+H+).

Amino Acid Analysis: Peptide Content: 65.27%

EXAMPLE 2

N-[N-[4-[[4-(aminoiminomethyl)phenyl]amino]-1,4-dioxobutyl]-L-alpha-aspartyl]-L-phenylalanine

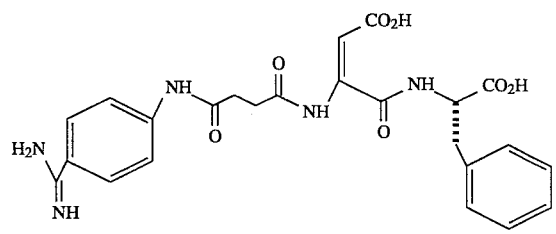

N-[N-[4-[[4-(aminoiminomethyl)phenyl]amino]- 1,4-dioxobutyl]-L-α-aspartyl-L-phenylalanine, 1-methyl ester prepared in Example 1, Step 2 (700 mg) was added to water/acetonitrile (20 ml) followed by lithium hydroxide (100 mg) at 25 C. The mixture was stirred for 30 min. The course of the reaction was monitored by RPHPLC. After satisfactory diacid was formed the reaction was neutralized with TFA and purified by reverse phase chromatography (water/acetonitrile) to result in 460 mg of a white solid: 1H NMR (d6-DMSO) δ2.47 (m, 4H), 2.65 (m, 3H), 2.97 (m, 2H), 4.45 (m, 1H), 4.58 (m, 1H), 7.79 (s, 4H), 7.99 (d, 1H, J=8.09 Hz), 9.1 (bs, 2H), 9.19 (bs, 2H), 10.42 (s, 1H); MS (FAB) M/e 498.3 (M+H+).

Elemental Analysis Required for C24 H22N5O7.F3C2O2H.H2O C 48.99 H 4.86 N 10.90 Found C 49.11 H 4.58 N 10.69

EXAMPLE 3

Cyclopentyl 3S-[[4-[[4-(aminoiminomethyl)phenyl]amino]-1,4-dioxobutyl]amino]-4-oxo-4[(2-phenylethyl)amino]butanoate

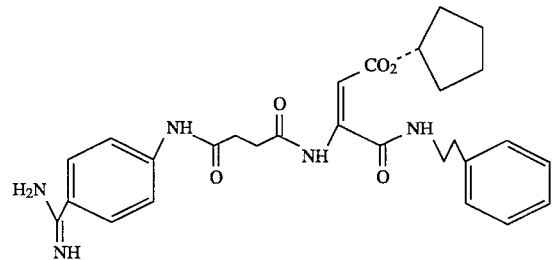

Step 1. Preparation of t-butyl 3-[[4-[[4-(aminoiminomethyl)-phenyl]amino]-1,4-dioxobutyl]amino]-4-oxo-4-[(2-phenylethyl)amino]butanoate.

The title compound is prepared in the manner of Example 1, Step 1 substituting Asp(O-t-butyl)-2-phenethyl amide for Aspartame.

Step 2. Preparation of 3-[[4-[[4-(aminoiminomethyl)-phenyl]amino]-1,4-dioxobutyl]amino]-4-oxo-4-[(2-phenylethyl)amino]butanoic acid.

A mixture of the compound prepared in Example 3 Step 1 (390 mg), trifluoroacetic acid (9 mL), and water (1 mL) is stirred at 23° C. for 1 h, and then evaporated under a slow nitrogen stream overnight. The product is purified on a reverse-phase C-18 functionalized silica gel column (1.9 cm×15 cm) using a linear gradient of 10% methanol/water 0.5% acetic acid to 100% methanol (40 min) with a flow rate of 3 mL/min to afford the title compound. The product purity is verified by H NMR, C NMR, and fast atom bombardment mass spectrometry.

Step 3. Preparation of cyclopentyl 3S-[[4-[[4-(aminoiminomethyl)-phenyl]amino]-1,4-dioxobutyl]amino]-4-oxo-4-[(2-phenylethyl)amino]butanoate.

3-[[4-[[4-(Aminoiminomethyl)phenyl]amino]-1,4-dioxobutyl]amino]-4-oxo-4-[(2-phenylethyl)amino]butanoic acid is activated with DSC in DMF and an excess of cyclopentanol is added. After the end of reaction (as monitored by HPLC), the title product is isolated by preparative HPLC and lyophilized to a white powder.

EXAMPLE 4

N-[N-[[2-[[[4-(aminoiminomethyl)phenyl]amino]carbonyl]cyclohexyl]carbonyl]-L-alpha-aspartyl]-L-phenylalanine, 1-methyl ester.

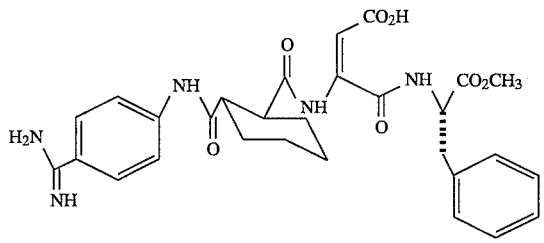

Step 1. Preparation of [2-[[[4-(aminoiminomethyl)phenyl]amino]carbonyl]cyclohexyl]carboxylic acid A mixture of 10 g trans-1,2-cyclohexanedicarboxylic anhydride (0.065 mol), 13.7 g (0.065 mol) aminobenzamidine hydrochloride, 100 mL of pyridine and 100 mL of dimethylformamide was stirred at 100° C. for 3 h.

The reaction mixture was concentrated in vacuo, brought to pH 7 with 0.5 N sodium hydroxide and water (total volume 200 mL). Upon cooling, a precipitate appeared that was filtered (14 g): $^1$H NMR (DMSO) δ1.3 (bs, 4H), 1.75 (bs, 2H), 2.2 (bs, 2H), 2.5 (bs, 2H), 7.8 (s, 4H), 9.1 (bs, 2H), 9.2 (bs,2H); 10.4 (s,1H); MS (FAB) m/e 290.1(M+H+). The material was dissolved in aqueous HCl and lyophilized to a white powder.

Step 2. Preparation of N-[N-[[2-[[[4(aminoiminomethyl)phenyl]amino]carbonyl]cyclohexyl]carbonyl]-L-alpha-aspartyl]-L-phenylalanine, 1-methyl ester.

The acid prepared in step 1 is coupled to aspartame using the anhydride procedure similar to that described in Example 1, Step 1. After concentration in vacuo, the residue is purified by HPLC (H2O:ACN:0.05%TFA) on a linear H2O:ACN 5:95>70:30 over 25 min. The product is collected and its structure verified by H NMR, C NMR, and fast atom bombardment mass spectrometry.

EXAMPLE 5

N-[N-[4-[[4-(aminoiminomethyl)phenyl]amino]-1,4-dioxo-2E-butenyl]-L-alpha-aspartyl]-L-phenylalanine, 1-methyl ester.

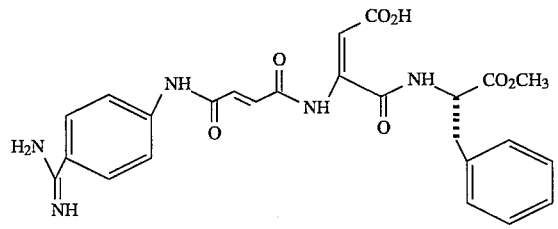

Step 1. Preparation of 4-[[4-(aminoiminomethyl)-phenyl]amino]-4-oxo-2E-butenoic acid.

In a round bottomed flask under a static atmosphere of dry nitrogen were mixed 1.4 g of monoethyl fumarate, 1.36 g of isobutyl chloroformate and 1.01 g N-methylmorpholine in 100 mL DMF. 4-aminobenzamidine dihydrochloride (2.06 g) and 2.02 g N-methyl-morpholine were added at room temperature and the reaction mixture was stirred at 25° C. for 30 min. Water and sodium hydroxide were added to pH 10 and after one hour stirring, neutralized to pH 7 to precipitate the zwitterion. Filtration provided 1 g of the desired compound as a white solid: $^1$H NMR (DMSO) δ 1.1 (t, 3 H, J =7 Hz), 2.45 (m, 2H), 2.6 (m, 2H), 2.75 (d, 2H, J=7 Hz), 4.0 (q, 2H, J =7 Hz), 4.2 (dd, 1H, J=7 Hz and 8 Hz), 7.3 (m, 4H), 7. 8 (s, 4H), 8.45 (d, 1H, J=8 Hz), 9.05 (bs, 2H), 9.2 (bs, 2H), 10.4 (s, 1H).

Step 2. Preparation of N-[N-[4-[[4(aminoiminomethyl)phenyl]-amino]-1,4-dioxo-2E-butenyl]-L-alpha-aspartyl]-L-phenylalanine, 1-methyl ester.

N-fumarylamino benzamidine prepared in Example 5, Step 1 is added to dry DMF (50 ml) followed by N-methylmorpholine and isobutyl chloroformate under nitrogen atmosphere. The mixture is stirred for 5 min and aspartame is added followed by N-methylmorpholine. After 2 h the solvents are removed under reduced pressure and the product is purified by reverse phase chromatography (water/acetonitrile) to give a light solid.

EXAMPLE 6

N-[N-[4-[[4-(aminoiminomethyl)phenyl]amino]-2(3)-methyl-1,4-dioxobutyl]-L-alpha-aspartyl]-L-phenylalanine, 1-methyl ester.

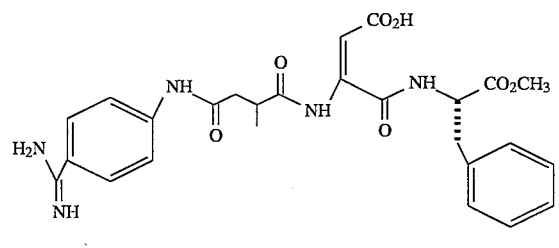

-continued

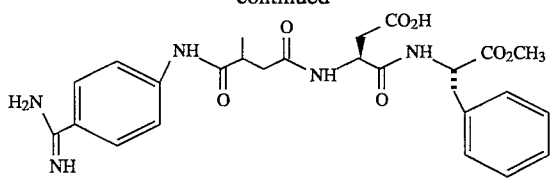

Step 1. Preparation of 4-[[4-(aminoiminomethyl)phenyl] amino]-2(3)-methyl-4-oxobutanoic acid A procedure similar to Step 1 of Example 1 using 5 g of aminobenzamidine di-HCl and 2.85 g methyl succinic anhydride was used. The product was filtered, washed with water, acetonitrile and ether. The white solid (4.5 g) was suspended in dioxane, 4N HCl in dioxane (100 ml) was added and the suspension was stirred for 1 h, filtered and dried.

Step 2. Preparation of N-[N-[4-[[4-(aminoiminomethyl)phenyl]-amino]-2(or 3)-methyl-1,4-dioxobutyl]-L-alpha-aspartyl]-L-phenylalanine, 1-methyl ester.

N-2(3)Methylsuccinimylamino benzamidine hydrochloride prepared in Step 1 is activated with isobutyl chloroformate and coupled with aspartame in a manner similar to Example 1, Step 2. Following a procedure similar to Example 1, Step 2 the reaction mixture is worked up and purified by reverse phase chromatography (water/acetonitrile). The two regioisomers are isolated as a white solid after lyophilization and the structures verified by $^{13}C$ and mass spectroscopy.

EXAMPLE 7

Preparation of 3S-[[4-[[4-(aminominomethyl)phenyl]-amino]-1,4-dioxobutyl]amino]-4-[[2-(1H-indol-3-yl)ethyl] amino]-4-oxobutanoic acid.

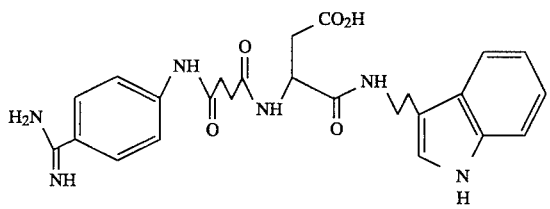

Step 1. Preparation of (O-t-Butyl) 3-[[4-[[4-(aminoiminomethyl)phenyl]amino]-1,4-dioxobutyl]amino]-4-[[2-(1H-indol-3-yl)ethyl]amino]-4-oxobutanoate.

The title compound is prepared in the manner of Example 3 substituting Asp(O-t-butyl)-2-(3-indolyl)ethyl amide for aspartame of Example 1. The product purity is verified by C NMR(CD3CO2D) and fast atom bombardment mass spectrometry.

Step 2. Preparation of 3S-[[4-[[4-(aminoiminomethyl)phenyl]-amino]-1,4-dioxobutyl[amino[-4-[[2-(1H-indol-3-yl)ethyl]amino]-4-oxobutanoic acid.

A mixture of compound prepared in Step 1 of Example 7 (390 mg), trifluoroacetic acid (9 mL), and water (1 mL) is stirred at 23° C. for 1 h, and then evaporated under a slow nitrogen stream overnight. The product is purified on a reverse-phase C-18 functionalized silica gel column (1.9 cm×15 cm) using a linear gradient of 10% methanol/water 0.5% acetic acid to 100% methanol (40 min) with a flow rate of 3 mL/min to afford the title compound. The product purity is verified by H NMR, C NMR, and fast atom bombardment mass spectrometry.

EXAMPLE 8

N-[N-[4-[[4-(aminoiminomethyl)-3-chlorophenyl]amino]-1,4-dioxobutyl]-L-alpha-aspartyl-L-phenylalanine, 1methyl ester.

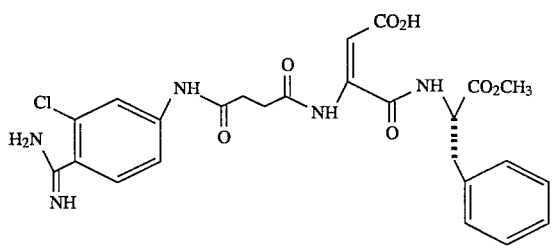

Step 1. Preparation of 4-[[4-(aminoiminomethyl)3-chlorophenyl]amino]-4-oxobutanoic acid hydrochloride To a mixture of 4-amino-2-chlorobenzonitrile (3.05 g, 20.0 mmol), diisopropylamine (5.0 mL, 30.0 mmol), and methylene chloride (20 mL) at 0° C. under nitrogen was added 3-carbomethoxypropionyl chloride (4.50 g, 30 0 mmol) dropwise over 3 min After 10 min at 0° C. the reaction mixture was allowed to warm up to 23° C. After 2h, the reaction mixture was concentrated in vacuo, diluted with ethyl acetate (150 mL), washed with 1N KHSO4 (1×80 mL), brine (1×80 mL), dried (Na2SO4), and concentrated in vacuo. The residue was diluted with ether (80 mL), filtered, and concentrated in vacuo. This procedure afforded material (4.5 g, 85%) of sufficient purity to be taken on to the next step without further purification.

The ester (4.0 g, 15 mmol) was hydrolyzed by treating with 1N NaOH:methanol (15 mL:60 mL) for 45 min. The reaction was concentrated in vacuo, diluted with 5% NaHCO3 (150 mL), and extracted with ethyl acetate (60 mL). The aqueous layer was acidified (pH1-2) with 1N KHSO4 and extracted with ethyl acetate (2×100 mL). After drying (MgSO4), the ethyl acetate was removed in vacuo to afford the free acid (3.1 g, 82%).

Hydrogen sulfide was bubbled through a solution of 4.00 g (15.9 mmol) of the above acid in pyridine: triethyl amine (24 mL:2.4 mL) for 5 minutes at 23° C. After 24 h at 23° C. in an enclosed flask, the reaction mixture was concentrated under a steady stream of nitrogen. The residue was diluted with ethyl acetate (300 mL), washed with KHSO4 (1N, 2×100 mL), brine (1×50 mL), and dried (Na2SO4). Concentration in vacuo afforded a quantitative mass recovery of the thioamide.

Thioamide (4.53 g, 15.8 mmol) was dissolved in a solution of acetone:iodomethane (28 mL:2 mL). The reaction mixture was warmed to achieve reflux for 40 minutes. Concentration in vacuo followed by trituration with ether and filtration afforded a quantitative yield of thiourea as the HI salt.

A solution of thioimidate (15.8 mmol) and ammonium acetate (1.83 g, 23.7 mmol) in methanol (10 mL) was warmed to achieve reflux for 4h. After cooling to 23° C., the reaction mixture was concentrated under a steady stream of nitrogen in the hood. The residue was dissolved in H2O (20 mL) and diluted with acetone (80 mL) to afford the zwitterion of 14 (2.53 g, 59.4%). The hydrochloride salt was formed by treatment with 6N HCl in dioxane (40 mL) for 1 h at 23° C. Concentration in vacuo afforded the hydrochloride salt which was azeotroped with benzene prior to use.

Step 2. Preparation of N-[N-[4-[[4-(aminoiminomethyl)-3-chlorophenyl]amino]-1,4-dioxobutyl]-L-alpha-aspartyl- L-phenylalanine, 1-methyl ester.

The title compound is prepared in the manner of example 1 using aspartame and the thioimidate prepared above (Step 1). The product is purified by reverse phase HPLC using the conditions of example 1 to afford the title compound. The product is verified by C NMR and Chemical Ionization Mass Spectrometry.

EXAMPLE 9

Preparation of N-[N-[4-[[4-aminoiminomethyl)phenyl] (phenylmethyl)amino]-1,4-dioxobutyl]-L-α-aspartyl]-L-phenylalanine.

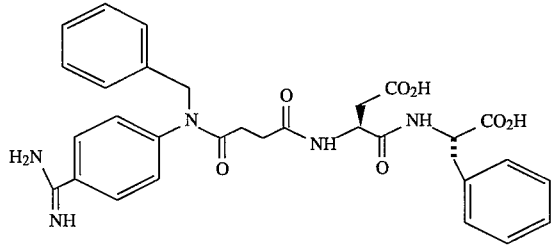

Step 1. A solution of 10.25 g. of 4-aminobenzonitrile in 50 mL pyridine was cooled to −30° C. and 14 mL trifluoroacetic anhydride was added with stirring over 15 minutes so as to maintain the temperature below −15° C. The mixture was then allowed to warm to 24° C. over 1 hour. After concentration under a slow stream of nitrogen overnight, the residue in ethyl acetate was washed with water, 5% hydrochloric acid, water and brine. After drying over sodium sulfate and evaporation of solvent, crystallization from ether-hexane provided 17.81 g. of N-trifluoroacetyl-4-aminobenzonitrile.

Step 2. (Note: method adapted from Johnstone, R. A. W.; Payling, D. W.; Thomas, C., J. Chem. Soc. (C) 1969, 2223–2224.) To a solution of 5.01 g. of the above amide and 11 mL of benzyl bromide in 50 mL of acetone was added 13.5 g. of dry potassium carbonate. The mixture was refluxed with vigorous stirring for 4 hours then cooled and the solids were removed by filtration. After evaporation of solvents the residue was chromatographed by the Flash method of Still (Still, W. C.; Kahn, M.; Mitra, A. P., J. Org. Chem. 1978,43, 2923.) developing with ethyl acetate-hexane 4:1. The main fraction gave 6.02 g. of N-trifluoroacetyl-4-benzylaminobenzonitrile. Anal. Calcd. for $C_{16}H_{11}N_2OF_3$: C, 63.16; H, 3.64; N, 9.21. Found: C, 63.46; H, 3.64; N, 8.93. This was followed by a fraction which after crystallization from ether-hexane gave 0.43 g. of 4-(benzylamino)benzonitrile, mp 66–67° C. Anal. Calcd. for $C_{14}H_{12}N_2$: C, 80.74; H, 5.81; N, 13.45. Found: C, 80.49; H, 5.81; N, 13.35.

Step 3. To a solution of 6.02 g. of N-trifluoroacetyl-4-benzylaminobenzonitrile in 50 mL of methanol was added 20 mL of 1 N sodium hydroxide. After 30 minutes of stirring, the mixture was concentrated in vacuo to remove the methanol. The product was extracted into ethyl acetate and the extract was washed with water and brine. After drying over sodium sulfate the solvent was evaporated and the residue crystallized from ether-hexane to yield 3.94 g. of 4-(benzylamino)benzonitrile identical to that above.

Step 4. A solution of 1.94 g. of 4-(benzylamino)benzonitrile in 20 mL tetrahydrofuran was chilled in an ice bath and 9.3 mL of 1 N sodium bis(trimethylsilyl)amide in tetrahydrofuran was added, followed by 1 g. of succinic anhydride. After 2 hours stirring at 25° C. solvents were evaporated under a nitrogen stream and the residue in ethyl acetate was extracted with water and 3% sodium carbonate. The combined aqueous layers were acidified with 5% hydrochloric acid. The crude solid was filtered off, washed with water, and dried. Flash chromatography developing with ethyl acetate-hexane 1:1 with a trace of acetic acid followed by crystallization of the main product from ethyl acetate-ether gave 0.41 g. of 4-[(4-cyanophenyl)(phenylmethyl)amino]-4-oxobutanoic acid mp 174°–175° C. Anal. Calcd for $C_{18}H_{16}N_2O_3$: C, 70.12; H, 5.23; N, 9.08. Found: C, 69.97; H, 5.25; N, 9.04.

Step 5. To a suspension of 80 mg of 4-[(4-cyanophenyl)(phenylmethyl)amino]-4-oxobutanoic acid and 115 mg of aspartylphenylalanine di tert-butyl ester in 5 ml of ethyl acetate was added 60 mg of dicyclohexyl carbodiimide. After being stirred for 2 hours at 25° C. the mixture was chilled overnight and the solid was removed by filtration. The filtrate was concentrated and the residue chromatographed (Flash) developing with ethyl acetate hexane, 3:2 to provide 116 mg of product. This material was dissolved in 2 mL of pyridine and 0.2 mL of triethylamine and the solution was saturated with hydrogen sulfide, stoppered and stirred for 68 hours at room temperature. The solvents were evaporated under a nitrogen stream and the residue in ethyl acetate was washed with 1 M potassium hydrogen sulfate, water and brine. Drying over sodium sulfate concentration left a residue of 133 mg. A solution of this material in 5 mL of acetone and 1 mL of iodomethane was refluxed for 30 minutes and concentrated to dryness. To this residue (154 mg) was added 50 mg of ammonium acetate and 10 ml of methanol. After refluxing for 3 hours the solvent was evaporated under nitrogen and the residue triturated with ether to leave 97 mg. This material was stirred in 1 mL of 90% trifluoroacetic acid - water for 1 hour and solvents evaporated to leave 91 mg of crude solid, which was chromatographed on a PLC-20 column packed with YMC-Gel® ODS-AQ 120-S50. The product was eluted in a gradient of methanol-water-acetic acid from 30:70:1 to 50:50:1, to provide 46 mg of N-[N-[4-[[4-aminoiminomethyl)phenyl] (phenylmethyl)-1,4-dioxobutyl]amino]-L-α-aspartyl]-L-phenylalanine, after concentration and lyophilization from water. Anal. Calcd. for $C_{31}H_{33}N_5O_7 \cdot C_2H_4O_2 \cdot 0.4\ H_2O$: C, 60.52; H, 5.82: N, 10.69. Found: C, 60.72; H, 5.90; N, 10.62.

The platelet-binding inhibitor activity of the compounds of the present invention can be demonstrated by the assays presented below.

FIBRINOGEN BINDING ASSAY

Fibrinogen binding was performed essentially as described by Plow et al., Blood 70, 110–115 (1987). Briefly, blood from humans who had not been given any antiplatelet drugs in the previous two weeks was collected into 1/10th volume of CCD buffer (100 mM sodium citrates, 136 mM glucose, pH 6.5). The blood was centrifuged for 3 min at 1000×g and platelet rich plasma was transferred to a plastic tube with a plastic pipet and placed on ice. After 15 minutes, ½ volume of ice cold CCD buffer was added and the sample was centrifuged at 900×g for 10 min at 2° C. The supernatant was decanted and the platelet pellet was gently resuspended in ½ the original volume of ice cold modified Tyrode's buffer (137 mM NaCl, 2.6 mM KCl, 12 mM $NaHCO_3$, 5.5 mM glucose, 15 mM HEPES, 0.5% BSA, pH 7.4). After incubating for 30 minutes at 37° C., the platelet count was adjusted to $4\times10^8$ platelets/ml with modified Tyrode's buffer. To test samples (final concentration=$1\times10^8$ platelets/ ml) were added in sequence: ADP (10 μM), CaCl$_2$ (2 mM), test compound, and $^{125}$I-fibrinogen (0.3 μM) to the aforesaid final concentrations in a volume of 200 μl. The samples were incubated for 40 min at 37° C. and 50 μl aliquots were centrifuged at 8,000×g through a 20% sucrose solution (400 μl). The tubes were quick frozen and the tips containing the platelet pellet were cut and assayed for bound $^{125}$I-fibrinogen by gamma scintillation counting. Specific binding was determined in each test by subtracting from the total binding the amount of $^{125}$I-fibrinogen bound in the presence of a 60-fold excess of unlabeled fibrinogen. The potency of test compounds (IC$_{50}$) was determined as the concentration of compound required to inhibit 50% of $^{125}$I-fibrinogen binding.

IN-VITRO PLATELET AGGREGATION IN PRP

Healthy male or female dogs were fasted for 8 hours prior to drawing blood; then 30 ml whole blood was collected using a butterfly needle and 30 cc plastic syringe with 3 ml of 0.129 M buffered sodium citrate (3.8%). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×10$^8$ platelets per ml. 400 μl of the PRP preparation and 50 μl of the compound to be tested or saline were preincubated for 1 minute at 37° C. in a BioData aggregometer (BioData, Horsham, Pa.). 50 μl of adenosine 5'-diphosphate (ADP) (50 μm final concentration) was added to the cuvettes and the aggregation was monitored for 1 minute. All compounds are tested in duplicate. Results are calculated as follows:

Percent of control=[(maximal OD minus initial OD of compound) divided by (maximal OD minus initial OD of control saline)]×100. The % inhibition=100– (percent of control).

The assay results for the compounds of Examples 1 and 2 and their median inhibitory concentrations (IC$_{50}$) are recorded in Table I. IC$_{50}$'s (if a compound showed 50% inhibition) were calculated by linear regression of the dose response curve.

TABLE I

| Example | Dog PRP IC$_{50}$ Micro M | Fibrinogen Binding Assay IC$_{50}$ Micro M |
|---|---|---|
| 1 | 0.09 | 0.048 |
| 2 | 0.08 | |
| 9 | 0.35 | |

What is claimed is:

1. A compound of the formula

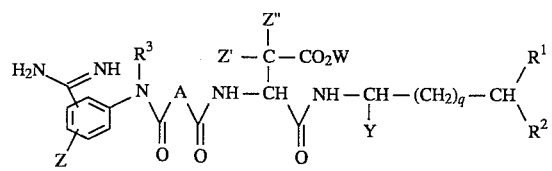

or a pharmaceutically acceptable salt thereof wherein

R$^1$, R$^2$ and R$^3$ are independently selected from the group consisting of hydrogen; alkyl having 1 to 6 carbon atoms; phenyl; substituted phenyl wherein each substituent can be selected from the group consisting of alkyl having 1 to 6 carbon atoms, trifluoromethyl, hydroxy, nitro and carboxyl; and a 5- or 6-membered heterocyclic ring fused to a benzene ring wherein the hetero atom is selected from the group consisting of nitrogen, oxygen and sulfur;

A is selected from the group consisting of ethylene, a lower alkenylene having 2 to 6 carbon atoms, lower alkynylene having 2 to 6 carbon atoms and a cycloalkylene having 3 to 6 carbon atoms, the ethylene, alkenylene, alkynylene or cycloalkylene optionally substituted by phenyl or phenyl substituted by halogen or hydroxy;

W is selected from the group consisting of hydrogen, methoxyalkyl, lower alkyl having 1 to 6 carbon atoms, and cycloalkyl having 3 to 6 carbon atoms;

Y is selected form the group consisting of hydrogen, carboxyl, and alkoxycarbonyl having 1 to 6 carbon atoms;

Z, Z' and Z'' are independently selected from the group consisting of halogen, alkoxy having 1 to 6 carbon atoms, alkyl having 1 to 6 carbon atoms, trifluoromethyl, hydrogen and hydroxy; and q is an integer from 0 to 3.

2. A compound according to claim 1 wherein R$^1$, R$^2$ and R$^3$ are independently selected from the group consisting of hydrogen, alkyl having 1 to 6 carbon atoms, phenyl, and substituted phenyl wherein each substituent can be selected from the group consisting of alkyl having 1 to 6 carbon atoms, halogen, alkoxy having 1 to 6 carbon atoms, trifluoromethyl, hydroxy, nitro and carboxyl.

3. A compound according to claim 2 wherein A is selected from the group consisting of ethylene, a lower alkenylene having 2 to 6 carbon atoms and lower alkynylene having 2 to 6 carbon atoms.

4. A compound according to claim 4 wherein Z, Z' and Z'' are independently selected from the group consisting of hydrogen and alkyl of 1 to 6 carbon atoms.

5. A compound of the formula

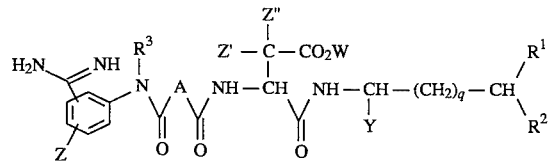

or a pharmaceutically acceptable salt thereof wherein

R$^1$, R$^2$ and R$^3$ are independently selected from the group consisting of hydrogen; alkyl having 1 to 6 carbon atoms; phenyl; and substituted phenyl wherein each substituent can be selected from the group consisting of alkyl having 1 to 6 carbon atoms, halogen, alkoxy having 1 to 6 carbon atoms, trifluoromethyl, hydroxy, nitro and carboxyl;

A is ethylene;

W is selected from the group consisting of hydrogen, methoxyalkyl, lower alkyl having 1 to 6 carbon atoms, and cycloalkyl having 3 to 6 carbon atoms;

Y is selected form the group consisting of hydrogen, carboxyl, and alkoxycarbonyl having 1 to 6 carbon atoms;

Z, Z' and Z" are independently selected from the group consisting of hydrogen and alkyl having 1 to 6 carbon atoms; and q is an integer from 0 to 3.

6. A compound according to claim 5 which is N-[N-[4-[[4-(aminominomethyl)phenyl]amino]- 1,4-dioxobutyl]-L-α-aspartyl]-L-phenylalanine, 1-methyl ester.

7. A compound according to claim 5 which is N-[N-[4-[[4-(aminoiminomethyl)phenyl]amino]- 1,4dioxobutyl]-L-α-aspartyl]-L-phenylalanine.

8. A pharmaceutical composition comprising a compound of the formula

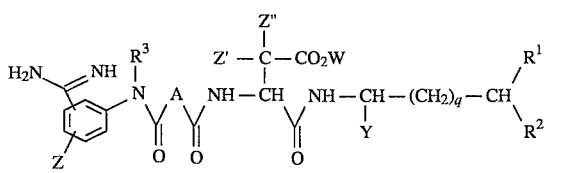

or a pharmaceutically acceptable salt thereof wherein $R^1$, $R^2$ and $R^3$ are independently selected from the group consisting of hydrogen; alkyl having 1 to 6 carbon atoms; phenyl; substituted phenyl wherein each substituent can be selected from the group consisting of alkyl having 1 to 6 carbon atoms, halogen, alkoxy having 1 to 6 carbon atoms, trifluoromethyl, hydroxy, nitro and carboxyl; and a 5- or 6-membered heterocyclic ring fused to a benzene ring wherein the hetero atom is selected from the group consisting of nitrogen, oxygen and sulfur;

A is selected from the group consisting of ethylene, a lower alkenylene having 2 to 6 carbon atoms, lower alkynylene having 2 to 6 carbon atoms and a cycloalkylene having 3 to 6 carbon atoms, the ethylene, alkenylene, alkynylene or cycloalkylene optionally substituted by phenyl or phenyl substituted by halogen or hydroxy;

W is selected from the group consisting of hydrogen, methoxyalkyl, lower alkyl having 1 to 6 carbon atoms, and cycloalkyl having 3 to 6 carbon atoms;

Y is selected from the group consisting of hydrogen, carboxyl, and alkoxycarbonyl having 1 to 6 carbon atoms;

Z, Z' and Z" are independently selected from the group consisting of halogen, alkoxy having 1 to 6 carbon atoms, alkyl having 1 to 6 carbon atoms, trifluoromethyl, hydrogen and hydroxy;

q is an integer from 0 to 3;

a pharmaceutically acceptable carrier.

9. A pharmaceutical composition according to claim 8 wherein $R^1$, $R^2$ and $R^3$ are independently selected from the group consisting of hydrogen, alkyl having 1 to 6 carbon atoms, phenyl, and substituted phenyl wherein each substituent can be selected from the group consisting of alkyl having 1 to 6 carbon atoms, halogen, alkoxy having 1 to 6 carbon atoms, trifluoromethyl, hydroxy, nitro and carboxyl.

10. A pharmaceutical composition according to claim 9 wherein A is selected from the group consisting of ethylene, a lower alkenylene having 2 to 6 carbon atoms and lower alkynylene having 2 to 6 carbon atoms.

11. A pharmaceutical composition according to claim 10 wherein Z, Z' and Z" are independently selected from the group consisting of hydrogen and alkyl of 1 to 6 carbon atoms.

12. A pharmaceutical composition comprising a compound of the formula

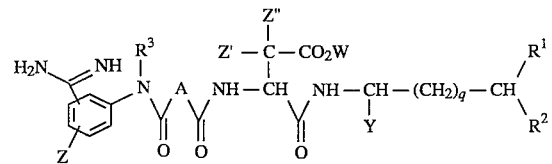

or a pharmaceutically acceptable salt thereof wherein $R^1$, $R^2$ and $R^3$ are independently selected from the group consisting of hydrogen, alkyl having 1 to 6 carbon atoms, phenyl, and substituted phenyl wherein each substituent can be selected from the group consisting of alkyl having 1 to 6 carbon atoms, halogen, alkoxy having 1 to 6 carbon atoms, trifluoromethyl, hydroxy, nitro and carboxyl;

A is ethylene;

W is selected from the group consisting of hydrogen, methoxyalkyl, lower alkyl having 1 to 6 carbon atoms, and cycloalkyl having 3 to 6 carbon atoms;

Y is selected form the group consisting of hydrogen, carboxyl, and alkoxycarbonyl having 1 to 6 carbon atoms;

Z, Z' and Z" are independently selected from the group consisting of hydrogen and alkyl having 1 to 6 carbon atoms;

q is an integer from 0 to 3; and a pharmaceutically acceptable carrier.

13. A pharmaceutical composition according to claim 12 wherein the compound is N-[N-[4-[[4-(aminoiminomethyl)phenyl]amino]- 1,4-dioxobutyl]-L-α-aspartyl]-L-phenylalanine, 1-methyl ester.

14. A pharmaceutical composition according to claim 12 wherein the compound is N-[N-[4-[[4-(aminoiminomethyl)phenyl]amino]- 1,4-dioxobutyl]-L-α-aspartyl]-L-phenylalanine.

* * * * *